(12) United States Patent
DiSpirito et al.

(10) Patent No.: US 7,199,099 B2
(45) Date of Patent: Apr. 3, 2007

(54) METHANOBACTIN: A COPPER BINDING COMPOUND HAVING ANTIBIOTIC AND ANTIOXIDANT ACTIVITY ISOLATED FROM METHANOTROPHIC BACTERIA

(75) Inventors: Alan A. DiSpirito, Ames, IA (US); James A. Zahn, Harbor Beach, MI (US); David W. Graham, Lawrence, KS (US); Hyung J. Kim, St. Paul, MN (US); Michail Alterman, Lawrence, KS (US); Cynthia Larive, Lawrence, KS (US)

(73) Assignees: The University of Kansas, Lawrence, KS (US); Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 10/741,831

(22) Filed: Dec. 19, 2003

(65) Prior Publication Data

US 2004/0171519 A1    Sep. 2, 2004

Related U.S. Application Data

(60) Provisional application No. 60/434,873, filed on Dec. 19, 2002.

(51) Int. Cl.
| | |
|---|---|
| A61K 38/08 | (2006.01) |
| C07K 7/04 | (2006.01) |
| C07K 2/00 | (2006.01) |
| C07K 1/14 | (2006.01) |
| A61K 38/00 | (2006.01) |
| A61K 38/02 | (2006.01) |
| A61K 38/10 | (2006.01) |

(52) U.S. Cl. ............ 514/6; 530/300; 530/329; 530/344; 514/2; 514/14; 514/15
(58) Field of Classification Search .......... 514/1, 514/2, 6; 530/300, 329
See application file for complete search history.

(56) References Cited

OTHER PUBLICATIONS

HJ Kim, et al. Science (2004), 305 (Sep. 10). 1612-1615.*
CM Tellez, et al. Isolation of Copper Biochelates . . . (1998) Appl. Environ. Micobiol. 64(3). 1115-1122.*
TK Wood. Active expression of soluble . . . (2002) Microbiology. 148(Nov. 2002). 3328-3329.*
JC Murrell. Expression of soluble . . . (2002) Microbiology. 148(Nov. 2002). 3329-3330.*
J-Y Xin, et al. Particulate methane . . . (2002) Biochem. Biophys. Res. Comm. 295. 182-186.*
HJ Kim, et al. Effects of oxygen . . . (2001) FEMS Micobiol. Letters. 201. 133-138.*
A. Gosslau and L. Rensing. Z. Gerentol. Gerlat. (2002) 35, pp. 139-150.*
H.J. Kim, et al. Chemtracts- Inorganic Chemistry (2005) 18, pp. 87-92.*
Alan A. DiSpirito, et al., Copper-Binding Compounds from *Methylosinus trichosporium* OB3b, Journal of Bicteriology, Jul. 1998, p. 3606-3613.
H de Groot, et al. "Tissue injury by reactive oxygen species and the protective effects of flavonoids" *Fundam Clin Pharmacol* 1998; 12:249-55, XP-001027003.
Zahn et al., "Membrane-Associated Methane Monooxygenase from *Methylococcus capsulatus* (Bath)", Journal of Bacteriology, vol. 178, No. 4, Feb. 1996, p. 1018-1029.

* cited by examiner

*Primary Examiner*—Cecilia J. Tsang
*Assistant Examiner*—Andrew D. Kosar
(74) *Attorney, Agent, or Firm*—McKee, Voorhees & Sease, P.L.C.

(57) ABSTRACT

A means and method for treating bacterial infection, providing antioxidant activity, and chelating copper using a copper binding compound produced by methanotrophic bacteria is described. The compound, known as methanobactin, is the first of a new class of antibiotics having gram-positive activity. Methanobactin has been sequenced, and its structural formula determined.

28 Claims, 3 Drawing Sheets

SEQUENCE LISTING

<160> NUMBER OF SEQ ID NOS: 1

<210> SEQ ID NO 1
<211> LENGTH: 4
<212> TYPE: PRT
<213> ORGANISM: methanotroph

```
<400> SEQUENCE: 1

Gly Ser Cys Tyr
 1
```

METHANOBACTIN: A COPPER BINDING COMPOUND HAVING ANTIBIOTIC AND ANTIOXIDANT ACTIVITY ISOLATED FROM METHANOTROPHIC BACTERIA

CROSS-REFERENCE TO RELATED APPLICATION

This invention claims priority to Provisional Patent Application Ser. No. 60/434,873 filed Dec. 19, 2002, the disclosure of which is hereby expressly incorporated by reference.

GRANT REFERENCE CLAUSE

This invention was funded in part by Department of Energy Grant No. 02-96ER20237. The government may have certain rights in this invention.

FIELD OF THE INVENTION

This invention relates to antibiotic and antioxidant compositions and methods of their use and manufacture. Specifically, this invention relates to pharmaceutical compositions including antibiotic and antioxidant compounds that may be isolated from methanotrophic bacteria.

BACKGROUND OF THE INVENTION

Methanotrophs are bacteria capable of using methane as their sole source of carbon and energy. These organisms oxidize methane by the following metabolic pathway:

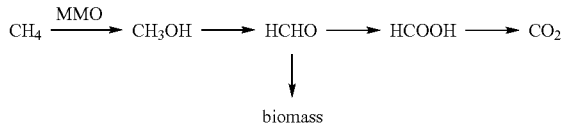

Microbial ecologists have long been interested in the methanotrophs due to their key role in the global methane cycle, oxidizing $CH_4$ to $CO_2$. The first step in this process is catalyzed by the enzyme methane monooxygenase (MMO), of which two forms are known: the particulate methane oxygenase (pMMO), a membrane-bound enzyme believed to be present in all methanotrophs, and the soluble methane monooxygenase (sMMO), a cytoplasmic enzyme present in only select species. Both forms of the enzyme oxidize a number of compounds, for instance, the common environmental contaminant trichloroethylene. Accordingly, this group of bacteria has attracted interest in regard to their potential for bioremediation.

In some genera of methanotrophs, either sMMO or pMMO is present depending on the copper concentration during growth. At low copper to biomass ratios, sMMO is expressed with low but detectable levels of the pMMO (Choi et al., 2003). At higher copper to biomass ratios, the pMMO is expressed exclusively. The polypeptides and structural genes for both enzymes have been characterized.

In spite of the central role of copper in the physiology of methanotrophs, the mechanism(s) of copper acquisition remains vague. Although true, a few studies have suggested the existence of a specific copper acquisition system in *M. capsulatus* Bath and *M. trichosporium* OB3b. The first indication of a specific copper uptake system was provided from phenotypic characterization of the constitutive sMMO mutants (sMMO$^C$) isolated by Phelps et al. (Phelps, P. A., et al. 1992) in *Methylosinus trichosporium* OB3b mutants having constitutive expression of soluble methane monooxygenase in the presence of high levels of copper. (Appl. Environ. Microbiol. 58:3701–3708). Fitch et al. found that in *M. trichosporium* OB3b, these sMMO$^C$ mutants were defective in copper uptake and showed preliminary evidence for an extracellular copper-complexing agent. Fitch, M. W., et al. 1993. Phenotypic characterization of copper-resistant mutants of *Methylosinus trichosporium* OB3b. Appl. Environ. Microbiol. 59:2771–2776. Working with the same mutants, Téllez et al. partially purified this copper-complexing agent and determined that it was a small molecule with a molecular mass of approximately 500 Da with an association constant with copper of $1.4 \times 10^{16} M^{-1}$. Téllez, C. M., et al. 1998. Isolation of copper biochelates from *Methylosinus trichosporium* OB3b and sMMO$^C$ mutants. Appl. Environ. Microbiol. 64:1115–1122.

Other evidence for a specific copper uptake system was provided by the copper-binding cofactor (CBC) from *M. capsulatus* Bath. Zahn, J. A., et al. 1996. The membrane-associated methane monooxygenase from *Methylococcus capsulatus* Bath. J. Bacteriol. 178:1018–1029. During the isolation of the pMMO from *M. capsulatus* Bath, methanobactin, initially called the copper-binding compound or CBC was identified in association with the purified enzyme, in the washed membrane fraction, and in the extracellular fraction. The CBC was determined to be a small polypeptide with a molecular mass of 1,232 Da. In *M. capsulatus* Bath, the cellular location of the CBC varied depending on the copper concentration in the culture medium and on the expression of the pMMO.

In a 1998 study, what were believed to be two separate copper-binding compounds (CBCs) were isolated from the spent media of both the wild type and a constitutive soluble methane monooxygenase (sMMO$^c$) mutant, PP319 of *Methylosinus trichosporium* OB3b. DiSpirito, A. A. et al. (1998), Copper-binding compounds from *Methylosinus trichosporium* OB3b, 180: 3606–3612. The CBCs were identified as small polypeptides with molecular masses of 1,218 and 779 Da for CBC-L$_1$, and CBC-L$_2$, respectively. The CBC from *M. trichosporium* OB3b was identical to the CBC previously identified during the isolation of the pMMO from *M. capsulatus* Bath.

It has now been determined that there is one primary CBC produced by methanotrophs that is involved in copper uptake from the environment. This CBC appears to be the same copper-complexing agent partially purified by Téllez et al. This extracellular molecule has surprisingly been found to have antibiotic and antioxidant properties in addition to copper-chelating properties. For the first time, the CBC has been properly sequenced, and its structural formula identified.

Accordingly, it is a primary objective of the present invention to provide compositions and methods for providing antibiotic activity against using a copper binding compound (methanobactin) that is produced by methanotrophic bacteria.

It is a further objective of the present invention to provide compositions and methods for providing antioxidant activity using methanobactin.

It is still a further objective of the present invention to provide compositions and methods for chelating copper using methanobactin.

The method and means of accomplishing each of the above objectives as well as others will become apparent from the detailed description of the invention which follows hereafter.

SUMMARY OF THE INVENTION

The invention describes a novel copper binding compound, methanobactin, that is produced by methanotropic bacteria. Methanobactin has been properly sequenced, and its structural formula determined. The compound is different from other known metal binding compounds and antibiotics. Methanobactin is the first of a new class of antibiotics that has activity at least against gram-positive bacteria, including vancomycin-resistant bacterial strains of *Staphylococcus aureus* X920, Bacillus, and *Enterococcus fecalus*. Methanobactin is also effective against gram-negative bacteria if administered in conjunction with a metal chelator, such as ethylene diamine tetraacetate (EDTA). Methanobactin has also been shown to be useful as an antioxidant.

Methanobactin also has a high affinity for copper and can chelate both soluble and surface bound copper. The compound has the unique property of being soluble in its copper-free state, but becomes much more hydrophobic, although still water soluble, once copper is bound. This permits the copper-free and copper-associated forms of the molecule to be separated by a variety of chromatography techniques using hydrophobicity separation.

DETAILED DESCRIPTION OF THE FIGURES

DETAILED DESCRIPTION OF THE PREFERRED EMBODIMENT

The present invention relates to the isolation and use of a unique copper binding compound from methanotrophs, now known as methanobactin. The invention is predicated upon the unexpected discovery that methanobactin has antibiotic and antioxidant properties. Methanobactin has also been found to be an effective copper chelating agent.

As used herein, the term "methanobactin" refers to any copper binding protein produced by a methanotroph. Although the most commonly-occurring form of methanobactin (~80%) and its associated structure is described in detail below, methanobactin is a non-ribosomal synthesized peptide (i.e. produced by a non-ribosome peptide synthase) and modified peptides are frequently observed. Because of this, the structure of methanobactin may vary slightly due to these "errors" or variations in synthesis. In fact, it was originally believed that methanotrophs produced two distinct CBCs, previously identified as $CBC-L_1$, and $CBC-L_2$. DiSpirito et al. (1998). However, it has now been determined that the $CBC-L_2$ identified in the 1998 study was actually an "erroneously synthesized" form of $CBC-L_1$. "Methanobactin" is therefore intended to encompass $CBC-L_1$, and variations of this copper binding compound caused by errors occurring during synthesis whereby the protein still has activity for its intended purpose, i.e. as an antibiotic, antioxidant, and/or copper-chelating agent. The present invention is also intended to include copper-bound and copper-free forms of methanobactin, as well as synthetic forms of the same.

As used herein the term "prophylaxis-effective amount" refers to a concentration of methanobactin that is effective in inhibiting or preventing infection and subsequent disease by bacteria. Likewise, the term "treatment-effective amount" refers to a concentration of methanobactin that is effective in treating infection in terms of preventing an increase in the concentration of bacteria, decreasing the concentration of bacteria, and/or "curing" or irradicating a bacterial infection.

Studies on the physiological role of CBC (methanobactin) indicate it is a component of a high-affinity copper uptake system in methanotrophs that express both forms of methane monooxygenase (MMO), namely sMMO and pMMO. Such methanotrophs include, but are not limited to, *Methylococcus* and *Methylosinus*. The compound has a unique structure consisting of a short peptide chain consisting of amino acids, modified amino acids and non-amino acid components. The structure of methanobactin is shown below:

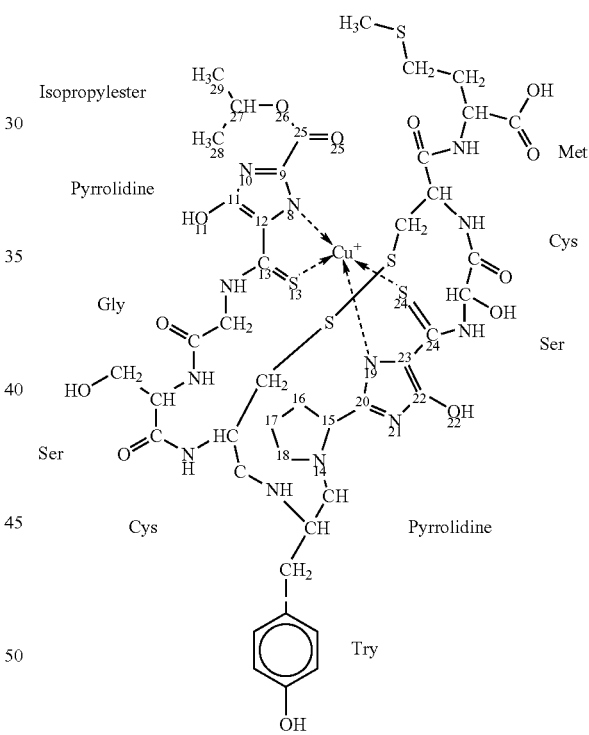

Figure 1:
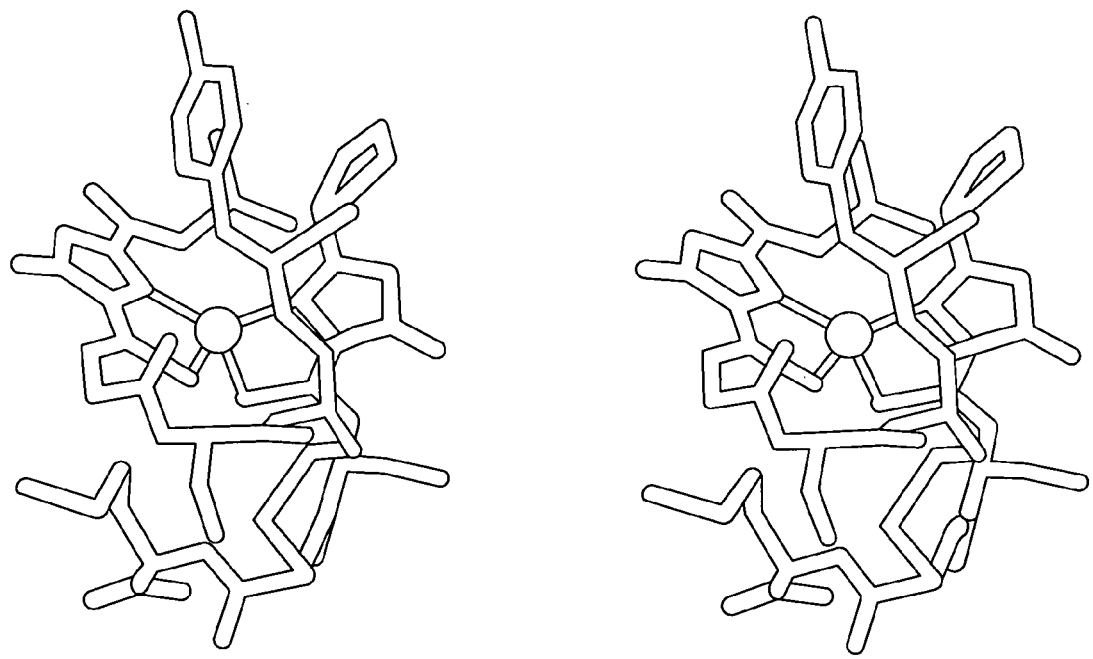
FIG. 1 is a stereo presentation of copper-containing methanobactin from *M. trichosporium* OB3b showing copper (ball) in center.
Figure 2:
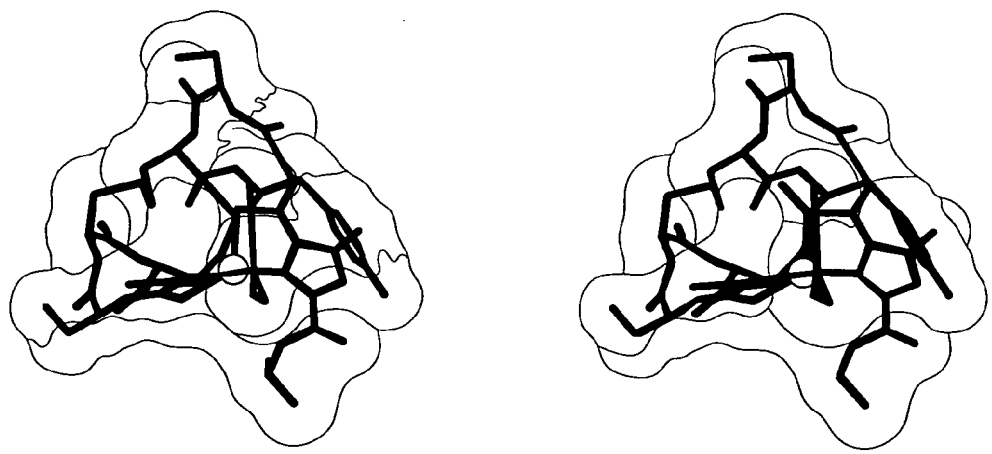
FIG. 2 is a stereoview of copper containing methanobactin using solvent-molecule interaction (probe interaction 1.4 Å).
Figure 3:
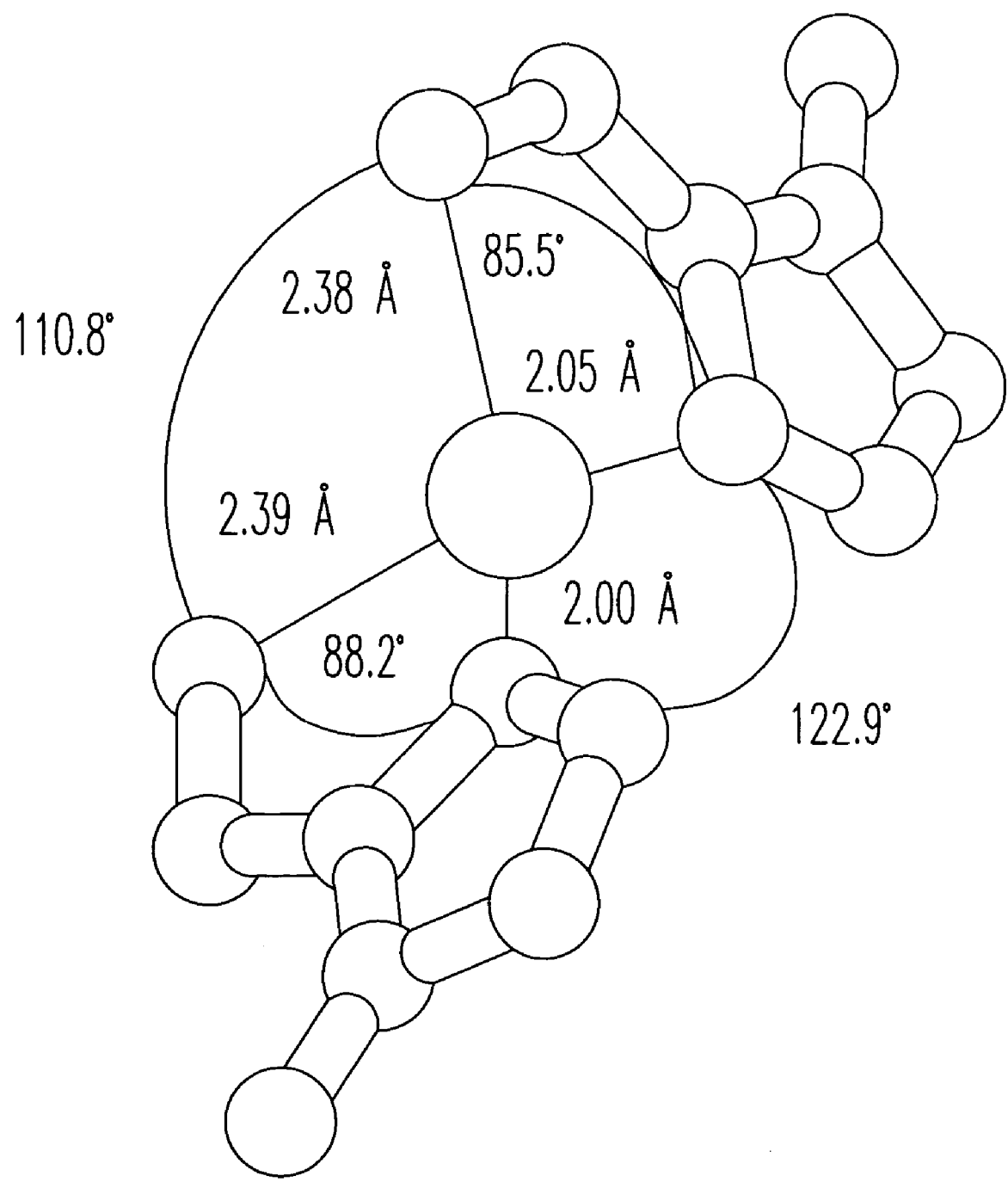
FIG. 3 is a copper coordination sphere of methanobactin showing tetrahedral geometry.

FIGS. 1–3 show the methanobactin molecule in other formats.

Methanobactin contains a tetrapeptide (Gly-Ser-Cys-Tyr) (SEQ ID NO:1) and a tripeptide (Ser-Cys-Met) linked together by two pyrrolidine-4-hydroxy-5-thiony-imidazole residues with the following sequence: N-2-isopropylester-(4-thionyl-5-hydroxy-imidazole)-Gly$^1$-Ser$^2$-Cys$^3$-Tyr$^4$-pyrrolidine-(4-thionyl-5-hydroxy-imidazole)-Ser$^5$-Cys$^6$-Met$^7$ (SEQ ID NO:2). All amino acids are L configuration with pyrrolidine as part of the peptide backbone. The chromopeptide chain of methanobactin contains two reverse turns. The first involves Gly$^1$-Ser$^2$-Cys$^3$-Tyr$^4$ (SEQ ID NO:1) residues (see above structural formula and FIG. 1) and resembles a type I "bend-like" turn, and the second reverse turn involves the pyrrolidine ring and resembles, with respect to its overall character, a type VI turn involving a cis-Pro residue at the i+2 position A disulfide linkage between the cysteine residues which holds the majority of the molecule in a ring.

The overall structural motif of the molecule is cyclic and the peptide backbone encloses the copper coordination sphere. However, the molecule is not an end-to-end cyclic chromopeptide. Rather, the cyclic backbone is conferred by the disulfide bridge from the cysteines located 4 residues apart and also by the coordination of copper with the two chromophores located 5 residues apart. The resulting three-dimensional motif therefore forms a "cage" around the copper coordination sphere and gives the molecule a very compact shape (FIGS. 1–3). Surface modeling of methanobactin using solvent-molecule interaction shows that the overall molecule can be described as having a general pyramidal shape with the copper coordination sphere located on the "bottom" of the pyramid. This metal complexation site was found to be essentially on the "underside" surface of the pyramidal base and not buried, although the isopropyl ester side chain obscures the metal site to a certain extent. The metal appears to be accessible only from this side of the molecule, which probably has functional implications. Its location could facilitate easy release of the ion without extensive conformational changes. The isopropyloxycarbonyl group folds underneath the bottom surface creating a "tail-like" projection and a cleft. The hydroxyl group of the $Ser^1$ side chain is located at the apex of the pyramid. The tyrosine side chain is surface exposed and its hydroxyl group is hydrogen bonded to a water molecule.

The copper-binding coordination sphere (FIG. 2) consists of two identical chromophoric moieties derived from 3-hydroxy-4-thionyl imidazole (imidazole thione) which is an unusual ligand for a natural compound. Both heterocycle rings along with the thionyl substituents are essentially co-planar. The ten individual atoms that comprise the thionyl imidazole deviate less than 0.03 Å from the least squares mean planes except for S(24) of chromophore B which deviates the most by 0.37 Å. The copper atom lies in the plane of chromophore B, but deviates by 0.87 Å from the plane of chromophore A. The $N^\epsilon(8)$-Cu—S(13) and $N^\epsilon(19)$-Cu—S(24) bond angles (ligand bite angles) of 85.5° and 88.2°, respectively, deviate the most from the ideal tetrahedral bond angle (109.5°). The Cu—S distances are 2.39 and 2.38Å for Cu—S(13) and Cu—S(24), respectively. The $N^\epsilon(8)$-Cu and $N^\epsilon(19)$-Cu distances are 2.01 and 2.05 Å, respectively.

The chelating groups that bind copper are the two $N^\epsilon$ atoms of the heterocycles and two S atoms of the thione substituents comprising an N,S-bidentate ligand system forming a distorted tetrahedral geometry. In terms of the geometry of copper-coordination complexes found in nature, the coordination sphere in methanobactin generally resembles the N,S-bidentate donor ligand, distorted tetrahedral system of blue copper proteins. However, the resemblance deviates significantly away from the geometry of the metal coordination sphere (besides the obvious difference in color due to differences in coordination electronic structures). Type I copper centers coordinate copper with the imidazole $N^\epsilon$ of histidine imidazole, whereas the N coordination in methanobactin are due to the non-amino acid derived imidazole.

The thionyl ligand (R—C═S) is also another unusual feature of methanobactin. In most blue copper proteins, the third and fourth coordination sites are the sulfur atoms of a cysteine side chain and a methionine side chain, respectively. In methanobactin, the sulfur atoms are thionyl substituents of the imidazole ring with relatively shorter distances to the copper ion when compared with the relatively long Cu—$S_{Met}$ bond distance of about 2.9 Å. In fact, all the copper to ligand bond distances suggests that the coordination bonds are relatively strong.

The N,S-donating ligand systems, where the sulfur is part of a thionyl (or thiol) group and the nitrogen is part of an imidazole, have not been found in nature. However, their synthetic counterparts exist and are synthesized due to their catalytic and pharmacological properties. For example, the antiulcer drug cimetidine (trade name, Tagamet®) contain a similar N,S-donating ligand system and binds copper (II) under in vivo conditions. Other N,S donor group ligands have shown activity against a variety of infections including bacterial and viral tuberculosis.

Overall, methanobactin structurally resembles the iron-binding siderophores, especially the pyoverdin class of siderophores, such as the pseudobactins from *Pseudomonas* sp. and the azotobactins from the *Azotobacter* sp. These compounds consist of a peptide backbone, along with a chromophoric moiety that takes part in metal coordination. Interestingly, in all pyoverdins, a serine residue, and in most cases two serine residues, are found in the peptide moieties. Glycine is also typically found in pyoverdins, which makes their overall resemblance similar, not only in overall motif, but in composition as well. The one striking difference in methanobactin is the presence of disulfide linkage along with the other sulfur-containing residues. It is likely that these sulfur residues play a critical role in the biological function of methanobactin. For example, copper containing methanobactin shows superoxide dismutase-like activity similar to or greater than that of superoxide dismutase or copper complexes designed or examined for this activity.

The crystal structure of methanobactin has revealed a molecule that is quite complex, especially for a compound of low molecular mass. Beyond its structural complexities, the molecule also contains a high degree of uniqueness, due especially to the presence of the chromophoric ligand and the pyrrolidine molecule. The number of sulfur atoms present, relative to the size of the molecule, is also unique and interesting, and their presence likely provides the molecule with a high level of biological activity. Methanobactin is the first known and characterized copper-chelating agent synthesized by a biological organism.

Methanobactin may be obtained by culturing a methanotroph capable of producing both sMMO and pMMO under conditions designed to induce production of the CBC, i.e. under conditions whereby the bacteria is under "copper stress." One method of inducing copper stress is by culturing the methanotroph in a medium that is copper-poor or copper free. In one embodiment of the invention, the methanotroph is cultured in a medium having a concentration of copper of about 1 μM or less (DiSpirito et al. 1998). Another means of providing copper-deficient conditions is through the use of mutant methanotrophs that are deficient in copper uptake, e.g. *M. trichosporium* OB3b.

In one embodiment of the invention, the methanotrophic bacteria is first cultured in a copper-containing medium which is subsequently diluted to a level sufficient to induce production of methanobactin. The culture medium begins to turn yellow once methanobactin production occurs due to the presence of the yellow methanobactin chromophore. The cells are harvested by centrifugation and the spent media collected on Dianion HP-20 columns and eluted with 60% methanol. The material eluted from the Dianion HP-20 columns is approximately 95–90% methanobactin. Final purification can be obtained on HPLC-chromatographs using reverse phase $C_{18}$ columns. Methanobactin can also be isolated from the washed membrane fractions of methanotrophs using N,N-dimethyl formamide as previously described (Zahn and DiSpirito. 1996. Membrane-associated Methane Monooxygenase from *Methylococcus capsulatus* (Bath). J. Bacteriol. 178:1018–1029.

Methanobactin has been found to have bacteriocidal activity against a number gram-positive bacteria including, but not limited to, *Staphylococci, Streptococci* and *Enterococci*. Methanobactin is also active against gram-positive bacteria that are resistant to other antibiotics, such as the two vancomycin resistant bacterial strains *Staphylococcus aureus* X920, *Enterococcus fecalus*, and vancomycin-resistant *Enterococcus faecium* (VRE), methicillin-resistant and methicillin-susceptible strains of *Staph aureus* (MRSA & MSSA).

Without intending to limit the invention to a particular mechanism of action, methanobactin acts as a respiratory uncoupler at low concentrations and as a respiratory inhibitor at higher concentrations. Based on its activity against gram-positive bacteria, methanobactin is useful in the treatment of various types of infections and infectious diseases including, but not limited to, colitis, antibiotic-associated diarrhea, entercolitis, bone and joint infections, septicemia, endocarditis, abscesses, uncomplicated skin and skin structure infections, pneumonia, meningitis, nosocomial infections, and perioperative infections.

Methanobactin has not been found to be effective against gram-negative bacteria by itself. Methanobactin, however, is bacteriocidal against gram negative bacteria when administered in combination with a metal chelator, such as EDTA, in a concentration of at least about 1:1 methanobactin to EDTA.

Methanobactin has also been found to provide protection from oxygen radicals, i.e. antioxidant activity. The structural characterization of Cu-methanobactin indicates that this molecule functions as an oxygen radical scavenger: i.e., the copper atom is in an open coordination sphere with a tetrahedral geometry on the surface of the molecule. Copper-free methanobactin has been found to have little to no superoxide dismutase-like activity, however, copper-containing methanobactin has superoxide dismutase-like activity similar to or greater than that of superoxide dismutase or copper complexes designed or examined for this activity.

Methanobactin has further been found to be effective as a copper-chelating agent, i.e. an agent that binds copper and removes it from solution. Copper-chelating agents have multiple uses. For instance, methanobactin may be used in the treatment of Wilson's Disease, an inherited disorder characterized by the liver's inability to metabolize copper, resulting in the accumulation of excessive amounts of copper in the brain, liver, kidney, cornea, and other tissues. The resulting copper accumulation and toxicity result in liver disease and cause brain damage in some patients.

Methanobactin may used in the same manner as other copper-chelating agents, such as D-penicillamine, trientine, bathocuproinedisulfonate (BCS), and captopril, in the treatment of Wilson's Disease, and other diseases and conditions that are treatable with copper-chelating agents, such as Alzheimer's Disease, in the reduction of tumor growth, and in reducing growth of yeast. Copper-chelators have also recently shown promise as a therapy for clogged arteries. (Lazar, M. et al. (May 23, 2003), Copper Chelation Represses the Vascular Response to Injury, Science Daily News Release, source: Maine Medical Center). Methanobactin may be used for the same purposes and in the same manner as other copper-chelating agents.

Methanobactin may be generally used for the prophylaxis and treatment of bacterial infections. It may also be used as an antioxidant and/or a copper chelating agent. Methanobactin is administered along with a pharmaceutically acceptable carrier. Any pharmaceutically acceptable carrier may be generally used for this purpose, provided that the carrier does not significantly interfere with the stability or bioavailability of the methanobactin.

Methanobactin can be administered in any effectively pharmaceutically acceptable form to warm blooded animals, including human and other animal subjects, e.g. in topical, lavage, oral, suppository, parenteral, or infusible dosage forms, as a topical, buccal, sublingual, or nasal spray or in any other manner effective to deliver the agents. The route of administration will preferably be designed to optimize delivery and/or localization of the agents to target cells.

In addition to the active compound, i.e. the methanobactin, the pharmaceutical compositions of this invention may contain suitable excipients and auxiliaries which facilitate processing of the active compounds into preparations which can be used pharmaceutically. Oral dosage forms encompass tablets, capsules, and granules, while dermatological preparations include creams, lotions, suspensions, sticks, etc. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

The formulation of pharmaceutically-acceptable dermatological and cosmetic preparations is well known in the art. Generally, cosmetic and dermatological preparations may comprise auxiliaries such as preservatives, bactericides, perfumes, substances for preventing foaming, dyes, pigments which have a coloring action, thickeners, surface-active substances, emulsifiers, softening, humidifying and/or humectant substances, fats, oils, and waxes. Other customary constituents of cosmetic and/or dermatological formulations include alcohols, polyols, polymers, foam stabilizers, electrolytes, organic solvents, and silicone derivatives.

If the formulation is a lotion, appropriate solvents that may be used are: 1) water or aqueous solutions; 2) oil, such as triglycerides of capric or caprylic acid; 3) fats, waxes and other naturally occurring and synthetic fat substances, preferably esters of fatty acids with alcohols of low C number, for example isopropanol, propylene glycol or glycerol, or esters of fatty alcohols with alkanoic acids of low C number or with fatty acids; 4) alcohols, diols, or polyols of low C number, and ethers thereof, preferably ethanol, isopropanol, propylene glycol, glycerol, ethylene glycol, ethylene glycol monoethyl, monoethyl or monobutyl ether, propylene glycol monomethyl, monoethyl or monobutyl ether, diethylene glycol monomethyl or monoethyl ether and analogous products. Mixtures of these solvents may also be used. Water can be a further constituent of alcoholic solvents.

Emulsions according to the invention may include, for example, the fats, oils, waxes, and other fatty substances set forth above, as well as water.

Ointments are generally water in oil preparations which may include hydrocarbon bases, such as petrolatum, and other oleaginous bases such as lard, benzoinated lard, olive oil, cottonseed oil, gelled mineral oil, and other oils.

Gels according to the invention usually comprise alcohols of low C number, for example ethanol, isopropanol, 1,2-propanediol, glycerol and water, or the above-mentioned oils in the presence of a thickener, which may be silicon dioxide or an aluminum silicate in oily-alcoholic gels and is preferably a polyacrylate in aqueous-alcoholic or alcoholic gels.

Solid sticks according to the invention may comprise, for example, naturally occurring or synthetic waxes, fatty alcohols or fatty acid esters.

Dermatological formulations which include methanobactin of this invention may further include a variety of substances, including suitable stabilizers, wetting, and dissolving agents as well as colorings, moisturizers, preservatives, and fragrances. These minors are added in small amounts and are conventionally known in pharmaceutical formulation work to enhance elegance. Such minors should comprise less than 1% of the overall composition. Dermatological formulations of this invention will generally include from about 0.5–25% by weight of the methanobactin, with about 2–10% by weight being preferred.

In addition to administration with conventional carriers, active ingredients may be administered by a variety of specialized delivery drug techniques which are known to those of skill in the art, such as portable infusion pumps.

The methanobactin compositions of the present invention are administered along with a pharmaceutically acceptable carrier in an amount sufficient to prevent bacterial infection, treat an active infection, provide antioxidant activity and/or copper-chelating activity. The methanobactin compounds of this invention have extremely low toxicity and a low degree of side effects even at high doses. The dosing range of the methanobactin compositions will vary depending on a number of factors, such as whether it is used for prophylaxis or treatment of an active infection, whether it used to provide an antioxidant effect, whether it is used as a copper-chelator, route of administration, dosing schedule, etc.

Methanobactin may be administered for antibiotic, antioxidant, and/or copper-chelation purposes in a dose ranging between 10–30 µg/ml in aqueous solution. In general, the therapeutic dose of methanobactin may range between about 0. 1–1000 mg/kg/day, with between about 1–100 mg/kg/day being preferred. The foregoing doses may be administered as a single dose or may be divided into multiple doses for administration. The methanobactin compositions may be administered once to several times daily. For prevention of bacterial infection, a typical dosing schedule could be, for example, 2.0–1000 mg/kg weekly beginning 1–2 weeks prior to exposure to the bacteria, taken up until 1–2 weeks post-exposure. When used in the prevention and treatment of gram-negative bacterial infection, methanobactin may be administered along with a concentration of EDTA or other metal chelator of about 1:1 to about 5:1, EDTA to methanobactin.

Use of methanobactin as an antioxidant offers the advantage of providing a degree of solubility between that of Vitamin C and Vitamin E. Thus, methanobactin is not excreted as quickly as very water-soluble Vitamin C, yet provides less of a risk of toxicity such as that associated with megadosing of highly hydrophobic Vitamin E.

Other drugs besides methanobactin which are compatible with the carrier ingredients may also be incorporated into the carrier. Such drugs may be readily ascertained by those of ordinary skill in the art and may include, for instance, other antibiotics, antioxidants, anti-inflammatory agents, antivirals, analgesics, etc.

It is understood that the present invention contemplates the use of not only methanobactin itself, but its prodrugs which metabolize to the compound and the analogues and biologically active salt forms thereof, as well as optical isomers which provide the same pharmaceutical results.

The present invention is also intended to not only include methanobactin produced from biological sources as already described above, but also synthetically-derived forms of the protein.

The following examples are offered to illustrate but not limit the invention. Thus, they are presented with the understanding that various formulation modifications as well as method of delivery modifications may be made and still be within the spirit of the invention.

EXAMPLE 1

Production and Purification of Methanobactin from *M. capsulatus* Bath

Materials and Methods

Organism and cultivation. *M. capsulatus* Bath and *M. trichosporium* OB3b are grown in nitrate mineral salts (NMS) media plus 0 µM, 0.2 µM, 0.5 µM, or 1.0 µM CuSO4, and a vitamin mixture at 42° C. and 37° C., respectively, under an atmosphere of 40% methane, 20% oxygen, and 40% (vol/vol/vol) air. Cells grown under low (i.e. no copper addition) copper conditions were cultured by a semi-continuous method using NMS plus a vitamin mixture under copper limitation at 37° C. in a 12-liter fermentor sparged at flow rates between 80 and 150 ml/minute methane and 2000 to 2500 ml/minute air.

Isolation of Washed Bacterial Membranes. All purification procedures were performed at 4° C. under anaerobic conditions unless otherwise stated. Cells were lysed in a French pressure cell at 18,000 lb/in². The homogenate was centrifuged at 12,000×g for 20 minutes to remove unlysed cells and debris. The supernate was then centrifuged at 140,000×g for 2 hours to sediment membranes. The supernate was discarded and the membranes resuspended using a Dounce homogenizer in buffer A containing 1 M KCl, and centrifuged for 2 hours at 140,000×g. The supernatant was discarded and the salt-washed membrane pellet was resuspended in 50 ml of buffer A using a Dounce homogenizer and stored under deoxygenated argon.

Isolation of copper-containing methanobactin from washed membrane. Salt-washed membranes were resuspended in 5 mM 3-[(3-cholamidopropyl)-dimethyl-ammonio]-1-propanesulfonate (CHAPS) with a Dounce homogenizer (final concentration of 30 mg protein/ml). The solution was centrifuged at 140,000×g for 2 hours and the supernate discarded. The pellet was resuspended in 20–30 times the pellet volume of 50% N,N-dimethyl formamide (DMF), and centrifuged at 13,000×g for 25 minutes. The supernate was saved and the pellet resuspended in 20–30 times the pellet volume of 100% DMF and centrifuged at 13,000×g for 25 minutes. The supernate was combined with the 50% DMF fraction and dried under vacuum on a rotary evaporator at 60° C. The sample was resuspended in a minimal volume of 50 mM phosphate buffer, pH 7.0 and loaded on a The spent media was loaded on either a 1.5×7 cm, a 2×11 cm or a 7×20 cm Diaion HP-20 column depending of the sample size. The column was washed with 2 column volumes of $H_2O$ and the organic phase was eluted from the Dianion HP-20 columns with 50% methanol: 50% acetonitrile (vol:vol). 2.5×20 cm silica gel (40–140 mesh) column. The sample was resuspended in a minimal volume of 50 mM phosphate buffer, pH 7.0 and loaded on a 2.5×20 cm silica gel (40–140 mesh) column. The column was washed with one column volume of $H_2O$, one column volume of 50% methanol and eluted with 50% methanol plus 20 mM HCl. The sample was freeze-dried and resuspended in buffer A.

Isolation of the copper-free methanobactin from spent media. Following centrifugation to remove whole cells the spent media is centrifuge a second time at 13,000×g for 20 minutes and the supernate loaded on a Diaion HP-20 (Supelco, Bellefonte, Pa.). The column is washed with 2 column volumes of $H_2O$ and the eluted from the Dianion HP-20 columns with 60% methanol: 40% $H_2O$ (vol:vol). The sample is approximately 85–95% methanobactin at this stage. Final purification is obtained by by chromatography on a reversed-phase (ex. Vyadec 218 TP1010 ($C_{18}$) equilibrated with 20% acetonitrile/10 mM sodium phosphate. A linear gradient of 20% acetonitrile/10 mM sodium phosphate to 60% acetonitrile/10 mM sodium phosphate is run and the eluate monitored at 392 and 345 nm.

Isolation of the copper-containing methanobactin from spent media. Following centrifugation to remove whole cells the spent media is centrifuged a second time at 13,000×g for 20 minutes and copper sulfate is added to the sup emate to a final concentration of 5 mM. The spent media is incubated for 1–8 hours at 4° C., centrifuged at 13,000×g for 15 min at 4° C. and filtered through Whatman 3MM filters and the filtrate loaded on a Diaion HP-20 (Supelco, Bellefonte, Pa.). The column is washed with 2 column volumes of $H_2O$ and the eluted from the Dianion HP-20 columns with 60% methanol: 40% $H_2O$ (vol:vol). The sample is approximately 85–95% methanobactin at this stage. Final purification is obtained by by chromatography on a reversed-phase (ex. Vyadec 218 TP1010 ($C_{18}$) equilibrated with 20% acetonitrile/10 mM sodium phosphate. A linear gradient of 20% acetonitrile/10 mM sodium phosphate to 60% acetonitrile/10 mM sodium phosphate is run and the eluate monitored at 392 and 345 nm. Methanobactin could also be isolated from spent media.

Mass spectrometry. The molecular mass of the copper-binding cofactor (cbc) was determined by time-of flight mass spectrometry on a Lasermat 2000 matrix-assisted laser desorption ionization (MALDI) mass spectrometer (Finnigan Corporation, San Jose, Calif.). Samples of the cbc were co-crystallized with the UV-absorbing matrix, super dihydroxyl benzoic acid (sDHB). The sDHB matrix consisted of 9 parts 2,5-dihydoxy benzoic acid and one part 2-hydroxy-5-methoxybenzoic acid solubilized in a solution of 70% acetonitrile, 0.1% trifluroacetic acid, and 29.9% $H_2O$. An excess of analyte (15 to 30 µg/µl) was mixed with the matrix solution in a one to one ratio and dried on a laser target grid before placing the target grid into the vacuum chamber.

EXAMPLE 2

Production and Purification of Methanobactin from Wild-Type *M. trichosporium* OB3b and sMMO[C] Mutants Materials and Methods Organisms and cultivation. Wild-type *M. trichosporium* OB3b and sMMO[C] mutants PP319 and PP358 were grown at 30° C. in nitrate mineral salts (NMS) medium plus 0.0 or 5.0 μM $CuSO_4$ under an atmosphere of 25% (V/V) methane and 75% (V/V) air. All cells were cultured by semicontinuous methods using a 3-liter fermentor (BIOFLO 3000; New Brunswick) sparged with methane and air in excess to maintain ambient oxygen concentrations at 75% saturation in air. A typical cell-culturing sequence involved culturing the cells in copper-free medium (no copper added) to an optical density at 600 nm ($OD_{600}$) of between 0.6 and 0.7. The culture was then diluted with fresh medium to an $OD_{600}$ of approximately 0.15 and cultured again to an OD of 0.7 to 0.75 before harvesting of 90% of the culture. At ODs of 0.6 and above, sMMO activities were measured prior to harvesting.

After harvesting, the remaining 10% of the culture was diluted with copper-free medium to an $OD_{600}$ of about 0.15, and the concentration of copper in the culture medium was raised to 5.0 μM for the subsequent copper-amended experiments. The culture was then grown to an $OD_{600}$ of 0.8 and diluted at least twice with medium containing 5 μM copper as described above prior to harvesting. The sMMO activity was monitored intermittently over this period. Wild-type cultures were harvested as before when no sMMO activity was detected for one dilution/growth cycle. Alternately, mutant cultures, which continually expressed sMMO activity in the presence of copper, were typically harvested after two dilution/growth cycles.

*M. capsulatus* Bath was grown in nitrate mineral salts medium plus 0 or 5 μM $CuSO_4$.

Induction of methanobactin in wild-type strains. Wild-type *M. trichosporium* OB3b and *M. capsulatus* Bath were cultured in 12-liter fermentors sparged at flow rates of 100 to 150 ml of methane per min and 2,000 to 2,500 ml of air per min in NSM plus 5 μM $CuSO_4$ at 42° C. for *M. capsulatus* Bath. When the culture reached an $OD_{600}$ of 0.8 to 1.1, 8 liters of the culture medium was removed and replaced with 8 liters of low-copper medium. If the culture developed a visual yellow color when cells reached an $OD_{600}$ of 0.8 to 1.2, the cells were harvested; if it did not, 8 liters of the culture was harvested and replaced with 8 liters of low-copper medium. These procedures were replaced until the medium developed a yellow color indicating the presence of methanobactin in the extracellular fraction.

Harvesting media and cells. Cells were harvested by centrifugation for 30 min at 9,000×g. The supernatant was decanted, collected, and filtered through a 0.22-μm-pore-size filter. The filtrate was either lyophilized or loaded on Sep-Pak cartridges (Millipore Corp., Bedford, Mass.) which had been pretreated with 10 ml each of ethanol, dichloromethane, ethanol, and $H_2O$. The methanobactin bound to the Sep-Pak cartridges were washed with 30 ml of $H_2O$ and 30 ml of 26 mM Tris-HCl-1 M urea and eluted with 0.2% (V/V) trifluoroacetic acid-99.8% (V/V) acetonitrile; the sample was then lyophilized.

Isolation of the methanobactin from spent media. (1) Method I. Lyophilized spent medium or lyophilized material extracted from Sep-Pak cartridges was resuspended in a minimal volume of 20 mM Tris-HCl (pH 8.0) plus 3 M urea and loaded on a 2.6 by 60-cm Superdex 30 (Pharmacia, Uppsala, Sweden) column equilibrated with 20 mM Tris-HCl (pH 8.0)-3 M urea. The yellow-colored sample migrated in three fractions with molecular masses of approximately 2,000 (P1), 1,000 (P2), and 500 (P3) Da. Each colored fraction was concentrated in a stirred cell (YC05 filter) and individually loaded on a 2.6-by 60-cm Superdex 30 column equilibrated with 20 mM Tris-HCl (pH 8.0)-3 M urea. The CBCs were then loaded separately on a 1- by 10-cm 15 RPC (Pharmacia) column equilibrated with 2 mM ammonium phosphate (pH 7.0) buffer. the sample was washed with four column volumes of 2 mM ammonium phosphate (pH 7.0) buffer, and the concentration of 2% (V/V) trifluoroacetic acid in acetonitrile increased to 75% over a 200-ml linear gradient. The methanobactin eluted at approximately 15% trifluoroacetic acid-2% acetonitrile mixture. The sample was lyophilized, resuspended in a minimal volume of $H_2O$, and run a second time on the 1- by 10-cm 15RPC column. The sample was then lyophilized and resuspended in $H_2O$.

(ii) Method II. Lyophilized spent medium or lyophilized material extracted from Sep-Pak cartridges was resuspended in a minimal volume of 20 mM Tris-HCl (pH 7.5)-50 KCl (buffer A) and loaded on a 2.6- by 20-cm Chelating Sepharose Fast Flow (FF) (Pharmacia Biotech) column equilibrated with buffer A. Prior to sample addition, the first 1.0 cm of the column was charged with $CuCl_2$, followed by a washing step with 2 column volumes of buffer A as described by Donat et al. Methanobactin bound to the column, and the sample was washed with 2 column volumes of buffer A. The concentration of buffer A plus 500 mM imidazole buffer (buffer B) was increased to 100% buffer B over a 500-ml linear gradient; methanobactin eluted at approximately 150 mM imidazole. The methanobactin column fractions were dialyzed and concentrated on a stirred cell (YC05 filter) and isolated individually following the column steps described for method I.

Isolation of the methanobactin from the washed membrane fraction. Methanobactin was also extracted from the washed membrane by using a 0.1% (V/V) HCl-N,N'-dimethyl formamide solution. The extraction was repeated until the extraction solution was clear. Following 0.1% HCl—N, N'-dimethyl formamide extraction, the N,N'-dimethyl formamide was evaporated under vacuum and the sample was resuspended in a minimal volume of 20 mM Tris-HCl (pH 8.0)-3 M urea and purified as described for method II.

Reconstitution of methanobactin with copper. As isolated by method II, methanobactin contained two copper ions. Methanobactin isolated from the spent medium by method I were copper-free. To these samples, copper was added as $CuCl_2$ solutions (1 to 200 μM) by titration, monitoring saturation by UV-visible absorption or electron paramagnetic resonance (EPR) spectroscopy.

Results

Isolation of methanobactin. Culture conditions for optimal production and purification of methanobactin from the spent media or from the washed membrane fractions of M. trichosporium OB3b are described in Materials and Methods. In wild-type *M. capsulatus* Bath and *M. trichosporium* OB3b, the concentration of methanobactin in the spent media was highest in cells expressing the pMMO and stressed for copper. Under these conditions, the spent media have a light yellow color due to the high concentration of methanobactin. Once the cells switch from expression of pMMO to expression of sMMO, the spent media becomes clear and the concentration of methanobactin in the spent media decrease by over 75%.

The two *M. trichosporium* OB3b $sMMO^C$ mutants, PP319 and PP358, have proven to be useful for the isolation of both methanobactin. In contrast to the wild-type strains, the concentrations of methanobactin in the culture media of the two $sMMO^C$ mutants did not significantly change with the concentration of copper in the culture media. The concentrations of methanobactin in the mutant strains remained similar (65 to 80%) to the levels observed in wild-type *M.* trichosporium OB3b cultured in low-copper medium-just before induction of the sMMO. Interestingly, also in contrast to wild-type strains, high concentrations of copper-containing methanobactin could be isolated from the spent copper-containing media of the two sMMO$^C$ mutants PP319 and PP358. In cells cultured in high-copper media, the high concentration of copper containing methanobactin in the medium of the two sMMO$^C$ mutants was evident by a bright yellow color. The color of the methanobactin becomes more intense with the binding of copper.

Separation of the concentrated spent media by gel filtration on a Superdex 30 column resulted in three distinct yellow-colored fractions with approximate molecular masses of 2,000 to 2,500, 1,000 to 1,500, and 500 to 750 Da. The concentration of each fraction varied with the preparation, but the fraction migrating in the 1,000–1,500-Da fraction (P2) was consistently the largest. The low-molecular weight fraction (P3) showed high conductivity. Each fraction was collected and purified by a second gel filtration and by reverse-phase chromatography as described in Materials and Methods.

All three yellow-colored fractions isolated from the spent medium from *M. trichosporium* OB3b bound iron as well as copper. Based on the molecular weights, N-terminal amino acid sequences, and spectral properties, the P1 and P3 fractions from the Superdex 30 column were determined to be breakdown products of the methanobactin isolated from the P2 fraction. This statement is based on the following observations. First, the results of N-terminal amino acid analysis for the P1 fraction were identical to those for methanobactin; however, the subunit molecular mass of P1 was 122 Da less than that of methanobactin. P1 migrated as a dimer on Superdex 30 gel filtration columns. Second, the lower molecular mass of P3 and the similarity in the first three amino acids from P3 to the first three amino acids of methanobactin suggest that P3 was the N-terminal fragment of methanobactin.

Solution properties of the methanobactin varied with metal binding and pH. Under acidic conditions (pH values below 6.5), methanobactin was very soluble and did not stick to reverse-phase columns such as 15RPC or C18. However, at neutral or alkaline pH values, or with the addition of copper, the methanobactin showed a tendency to bind to most low-pressure column resins tested in the absence of high (2 to 3 M) concentrations of urea.

EXAMPLE 3

Antioxidant Activity of Methanobactin

The $O_2^-$ scavenging properties of methanobactin were examined according to its ability to inhibit the reduction of nitroblue tetrazolium. Copper-free methanobactin has little to no superoxide dismutase-like activity, but Cu-methanobactin has superoxide dismutase or copper complexes designed or examined for this activity.

Materials and Methods

Organism and cultivation. *M. capsulatus* Bath cells cultured for enzyme isolations were grown in nitrate mineral salts medium (NMS) with 5 μM $CuSO_4$ and a vitamin mixture at 42° C. in shake flasks under an atmosphere of 30% methane and 70% air (V/V) to an optical density at 600 nm ($OD_{600}$) of 1.5 to 2.0. One liter of flask culture was used to inoculate 2 liters of medium in a 14-liter BioFlo fermentor (New Brunswick, Edison, N.J.). Cells were cultured in the fermentor at 42° C. and sparged at flow rates between 180 and 200 ml·min$^{-1}$ for methane and between 800 and 1,200 ml·min$^{-1}$ for air. The pH of the chemostat was maintained at 7.0 using potassium phosphate monobasic and sodium phosphate dibasic. When the culture reached an $OD^{600}$ of 1.8 to 2.0, the concentrations of copper and iron in the culture medium were increased continuously while maintaining an $OD^{600}$ of 1.8 to 2.0. The feed rate of the medium was set to double the culture volume every 10 to 12 h. Upon reaching a working volume of 10 liters, the system was operated as a chemostat. Media addition rate was adjusted to maintain a constant cell density between 1.8 and 2.0. Cells were harvested from continuous cultures by centrifugation at 14,000×g for 15 min at 4° C. and resuspended in 10 mM 4-[N-morpholino]propanesulfonic acid (MOPS)(pH 7.3) buffer followed by subsequent centrifugation at 14,000×g for 15 min. Washed cells were resuspended in 30 mM MOPS (pH 7.3)-1 mM benzamidine buffer.

Figure 4:
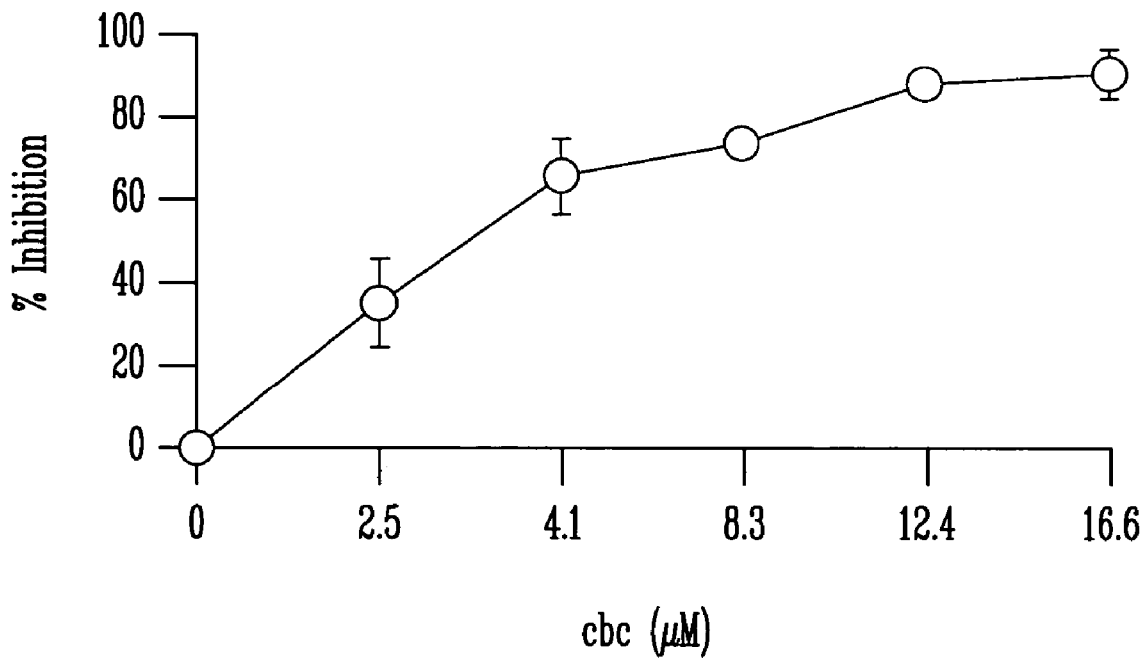
FIG. 4 is a graph illustrating the percent inhibition of nitroblue tetrazolium reduction in the presence of Cu-methanobactin (µM).

Superoxide dismutase-like activity of copper-containing methanobactin. Studies on the physiological role of cbc methanobactin indicate it is a component of a high-affinity copper uptake system in methanotrophs that express both forms of MMO. To test the oxygen radical scavenging activity of Cu-cbc, the compound was examined according to its ability to inhibit the reduction of nitroblue tetrazolium. (FIG. 4). Copper-free cbc has little to no superoxide dismutase-like activity, but Cu-cbc has superoxide dismutase-like activity similar to or greater than that of superoxide dismutase or copper complexes designed or examined for this activity.

EXAMPLE 4

Antibiotic Properties of Methanobactin

Materials and Methods

Organism and cultivation. *M. capsulatus* Bath cells cultured for enzyme isolations were grown in nitrate mineral salts medium (NMS) with 5 μM $CuSO_4$ and a vitamin mixture at 42° C. in shake flasks under an atmosphere of 30% methane and 70% air (V/V) to an optical density at 600 nm ($OD_{600}$) of 1.5 to 2.0. One liter of flask culture was used to inoculate 2 liters of medium in a 14-liter BioFlo fermentor (New Brunswick, Edison, N.J.). Cells were cultured in the fermentor at 42° C. and sparged at flow rates between 180 and 200 ml·min$^{-1}$ for methane and between 800 and 1,200 ml·min$^{-1}$ for air. The pH of the chemostat was maintained at 7.0 using potassium phosphate monobasic and sodium phosphate dibasic. The culture reached an $OD^{600}$ of 1.8 to 2.0. The feed rate of the medium was set to double the culture volume every 10 to 12 h. Upon reaching a working volume of 10 liters, the system was operated as a chemostat. Media addition rate was adjusted to maintain a constant cell density between 1.8 and 2.0. Cells were harvested from continuous cultures by centrifugation at 14,000×g for 15 min at 4° C. and resuspended in 10 mM 4-[N-morpholino]propanesulfonic acid (MOPS) (pH 7.3) buffer followed by subsequent centrifugation at 14,000×g for 15 min. Washed cells were resuspended in 30 mM MOPS (pH 7.3)-1 mM benzamidine buffer Gram Positive Activity Assays and Target Strains.

*Enterococcus fecalus* was cultured aerobically on Brain Heart Infusion broth at at 37° C., *Staphyloccus aureus*, *Escherichia coli*, X161, and *Bacillus thuringiensis* were cultured aerobically on Lauria-Burtani broth at 37° C., and *Listeria monocytogenes* was grown on Trypticase soy broth containing 0.6% yeast extract at 35° C. Minimum inhibitory concentrations were determined as previously described (A. F. Mendoca and S. J. Knabel. 1994. A novel strictly anaerobic recovery and enrichment system incorporating lithium for detection of heat-injured *Listeria monocytogenes* in pasteurized milk containing background microflora. Appl. Environ. Microbiol. 60: 4001–4008).

Oxygen uptake activity of washed cell suspensions was determined with a Clark oxygen electrode maintained at a constant water temperature of 37° C. Cell samples containing methanobactin were preincubated 5 minutes at 37° C. before the addition of substrate.

Isolation of the copper-containing methanobactin from spent media. Following centrifugation to remove whole cells the spent media is centrifuged a second time at 13,000×g for 20 minutes and copper sulfate is added to the supernate to a final concentration of 5 mM. The spent media is incubated for 1–8 hours at 4° C., centrifuged at 13,000×g for 15 min at 4° C. and filtered through Whatman 3MM filters and the filtrate loaded on a Diaion HP-20 (Supelco, Bellefonte, Pa.). The column is washed with 2 column volumes of $H_2O$ and the eluted from the Dianion HP-20 columns with 60% methanol: 40% $H_2O$ (vol:vol). The sample is approximately 85–95% methanobactin at this stage. Final purification is obtained by by chromatography on a reversed-phase (ex. Vyadec 218 TP1010($C_{18}$) equilibrated with 20% acetonitrile/10 mM sodium phosphate. A linear gradient of 20% acetonitrile/10 mM sodium phosphate to 60% acetonitrile/10 mM sodium phosphate is run and the eluate monitored at 392 and 345 nm.

Chemical analyses. Chemical analysis on crude and purified samples of methanobactin were performed by high-performance liquid chromatography electrospray ionization mass spectrometry (HPLC ES-MS) or by direct-injection electrospray mass spectrometry (ES-MS), or by tandem ES-MS-MS as described. For HPLC ES-MS experiments, ethanol-solubilized samples (50 µl) were separated on a Novapak C18 analytical column (3.9×100 mm) over a 30 minute linear gradient from 2% methanol plus 6.5 mM ammonium acetate (pH 5.5) to 90% methanol plus 6.5 mM ammonium acetate (pH 5.5) at a flow rate of 1 ml $min^{-1}$. The column effluent was split to a Finnigan Navigator (160 µl $min^{-1}$) equipped with a Finnigan electrospray source and to a Sedex 55 evaporative light scattering detector (ELSD; 840 µl $min^{-1}$; Alfortville, France) in order to provide qualitative and quantitative data, respectively. Ultraviolet and visible absorption spectra (190–550 nm) were acquired with a Series 1100 Hewlett Packard photodiode array spectrophotometer on column effluent prior to analysis by evaporative light scattering. The electrospray source was switched between positive and negative ion mode in 0.5 sec intervals to acquire both positive and negative ion spectra. During data acquisition, the MS probe was maintained at 3.6 kV, cone voltage was maintained at 36 V, the source temperature was held at 179° C., and drying gas flow was set at 505 $l·hr^{-1}$. MS tuning was performed daily using m-cresol purple. A standard mixture consisting of caffeine, m-cresol purple, and tylosin (100 µg/ml each) was injected at the beginning and at the end of analyses to assess instrument stability and performance.

Direct-injection electrospray mass spectrometry (ES-MS) was performed on SPE-treated samples using a Finnigan Navigator mass spectrometer equipped with a Finnigan electrospray source. MS instrument parameters were identical to those discussed above for the HPLC ES-MS analysis.

Exactly 50 µl of the sample was injected into the carrier gas stream of the electrospray source at a flow rate of 160 µl $min^{-1}$ using a Shimadzu LC-10ADVP liquid chromatograph pump. A standard consisting of m-cresol (50 µg/ml) was injected at the beginning and end of analyses to assess instrument stability and performance.

TABLE 1

Properties of purified methanobactin. Gram positive bacteriocidal activity of purified methanobactin.

| Property | Value |
| --- | --- |
| Yield (mg/l culture medium) | |
| Molecular Mass | |
| ES-MS positive ion (m/z) assignment | [M + H ]+ = 1217.3 |
| ES-MS negative ion (m/z) assignment | [M − H]− = 1215.4 |
| | 1216.4 |
| Assigned mass (Da) | |
| UV-VIS absorption maxima (nm) | 208, 264, 300, 344, 384, 401 (sh) |
| $^1$H-NMR Values | |
| Antimicrobial Activity | |
| *Micrococcus luteus* X186 (MIC, µg/ml) | 24 |
| *Enterococcus fecalus*, X690, vancomycin resistant (MIC, µg/ml) | |
| *Staphyloccus aureus*, X920, vancomycin resistant (MIC, µg/ml) | |
| *Candida albicans*, X657 | 0 |
| *Escherichia coli*, X161 | 0 |

EXAMPLE 5

Characterization of Methanobactin

Copper-Binding Compound from *M. trichosporium* OB3b. The three keys to the crystallization of this molecule were: (1) Isolation of cbc from spent media of cells in early log phase, yields are lower, but the presence of breakdown products are minimized. (2) The addition of copper to the spent media which stabilized the molecule, that is the copper containing cbc is more stable than copper free cbc. (3) Crystallization was obtained by the vapor diffusion method with of a near saturated solution of cbc in 60% acetylnitrile with ethyl acetate. Under these conditions copper, forms fibrous orange-yellow crystals. The color of the crystals was unexpected and gave the initial impression of an iron containing crystal However, ICP-MS, MS and structural analysis confirmed the cbc crystallized with copper atom.

Samples crystallized under copper excess defracted well and should yield a crystal structure close to 1Å resolution. The crystals grew from two stereoisomers. The basic structure has been determined and the preliminary two-dimensional representation is shown below (A). The sequence is: N-5-(-i-butylcarbonyl-chromophore)-gly-ser-cys-(4-methyl-phe)-pyrrolidine-chromophore-ser-cys-met (SEQ ID NO:3). The chromophore of cbc is 2-mercaptomethylene-3-hydroxy-pyrrole (B, shown below). Yellow to purple color of cbc comes from two pyrrole chromophores, which are responsible for coordinating the copper via N and S. The molecule contains two modified amino acids, the phe is modified with a methyl group on the ring (or a modified tyrosine) and a proline that is missing a carboxyl group.

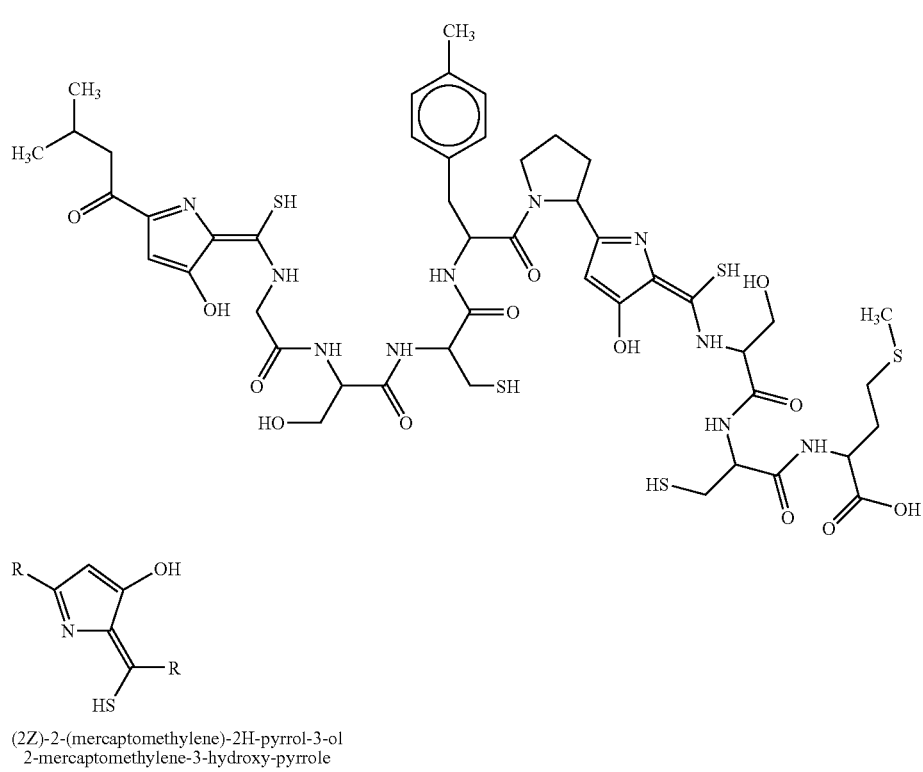

A.

B.

(2Z)-2-(mercaptomethylene)-2H-pyrrol-3-ol
2-mercaptomethylene-3-hydroxy-pyrrole

The sequence of cbc shows some similarity to metallothioneins. However in contrast to metallothioneins, the sulfur groups of the cysteines are not involved in metal-sulfur coordination, but in the formation an intermolecular disulfide bond. The overall structure of Cu-cbc is of a circular molecule with copper in the center in a four coordinated system by two S and two N on the chromophore.

The copper in the Cu-cbc crystals were electron paramagnetic resonance (EPR) silent, indicating the presence of Cu(I) or that the coppers were spin coupled. The second alternative appears less likely since the molecule only binds one copper atom and structure does not indicate the presence of dimers. Thus, the probable source of the EPR-silent copper associated with in the membrane fractions, in the membrane-associated methane monooxygenase (pMMO) and in preparations of cbc has been identified. Previous studies have demonstrated that 55 to 75% of the membrane-associated copper, pMMO-associated copper, and cbc-associated copper are EPR silent.

It should be appreciated that the methanobactin compositions of this invention may contain compositions within the scope of the formulas described above, or prodrugs or analogues of these compounds or a racemic mixture of either the D or the L form. The invention is also intended to include all biologically active salt forms of the compounds. Also, minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. An isolated copper binding protein having a sequence selected from the group consisting of N-2-isopropylester-(4-thionyl-5-hydroxy-imidazole)-Gly$^1$-Ser$^2$-Cys$^3$-Tyr$^4$-pyrrolidine-(4-thionyl-5-hydroxy-imidazole)-Ser$^5$-Cys$^6$-Met$^7$ and N-2-isopropylester-(4-thiocarbonyl-5-hydroxy-imidazolate)-Gly$^1$-Ser$^2$-Cys$^3$-Tyr$^4$-pyrrolidine-(4hydroxy-5-thiocarbonyl-imidazolate)-Ser$^5$-Cys$^6$-Met$^7$.

2. The copper binding protein of claim 1 having the following structure:

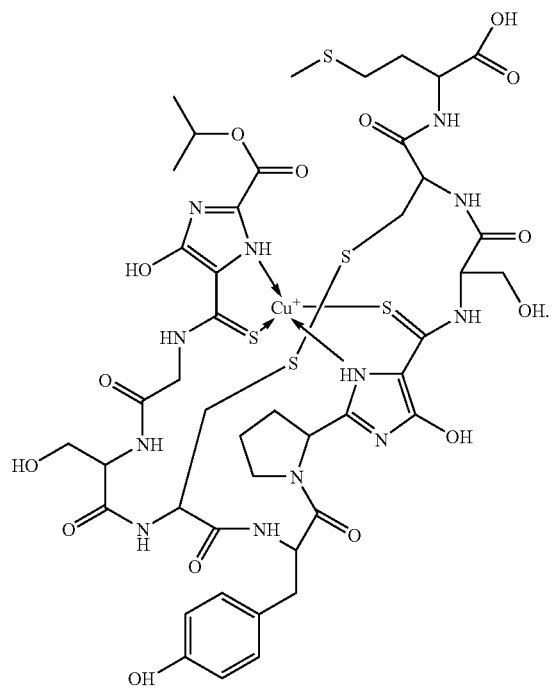

3. The copper binding protein of claim 1 having the following structure:

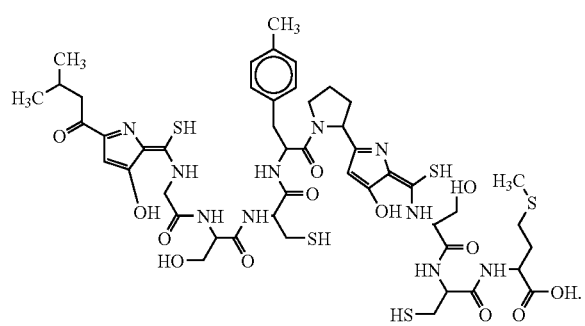

4. The copper binding protein of claim 1 that is isolated from a methanotroph.

5. The copper binding protein of claim 1 that is synthetic.

6. A pharmaceutical composition comprising: a copper binding protein methanobactin; and a pharmaceutically acceptable carrier, whereby the methanobactin has a sequence selected from the group consisting of N-2-isopropylester-(4-thionyl-5-hydroxy-imidazole)-Gly$^1$-Ser$^2$-Cys$^3$-Tyr$^4$-pyrrolidine-(4-thionyl-5-hydroxy-imidazole)-Ser$^5$-Cys$^6$-Met$^7$ and N-2-isopropylester-(4-thiocarbonyl-5-hydroxy-imidazolate)-Gly$^1$-Ser$^2$-Cys$^3$-Tyr$^4$-pyrrolidine-(4-hydroxy-5-thiocarbonyl-imidazolate)-Ser$^5$-Cys$^6$-Met$^3$.

7. The pharmaceutical composition of claim 6 whereby the methanobactin has the following structure:

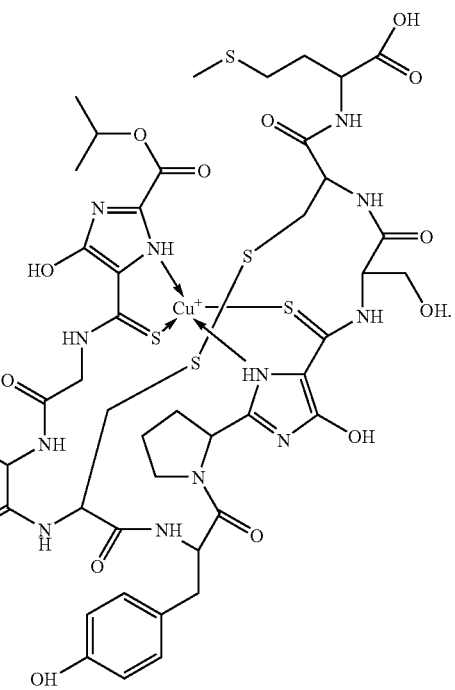

8. The pharmaceutical composition of claim 6 whereby the methanobactin has the following structure:

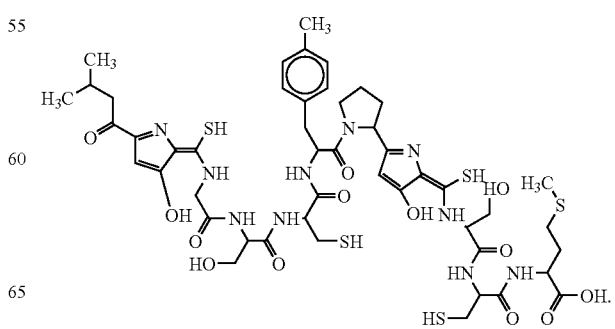

9. The pharmaceutical composition of claim 6 whereby the methanobactin is isolated from at least one methanotroph that produces both pMMO and sMMO.

10. The pharmaceutical composition of claim 6 whereby the methanobactin is synthetic.

11. The pharmaceutical composition of claim 6 that is suitable for administration by a method selected from the group consisting of oral, subcutaneous, intravenous, intranasal, rectal, sublingual, buccal, and topical.

12. A method of treating a bacterial infection comprising: administering a bacterial treatment effective amount of the copper binding protein of claim 1.

13. The method of claim 12 wherein the copper binding protein is administered in a dose of between about 0.1–1000 mg/kg/day.

14. The method of claim 13 wherein the copper binding protein is administered in a dose of between about 1–100 mg/kg/day.

15. The method of claim 12 wherein the copper binding protein is administered in a single dose.

16. The method of claim 12 wherein the copper binding protein is administered in divided doses.

17. The method of claim 12 wherein the copper binding protein is administered for a time period of at least 5 days.

18. The method of claim 12 wherein the copper binding protein is administered for treatment of a gram-positive bacterial infection.

19. The method of claim 12 wherein the copper binding protein is co-administered with a metal chelator for treatment of a gram-negative bacterial infection.

20. The method of claim 19 wherein the metal chelator is EDTA.

21. The method of claim 19 whereby the copper binding protein is co-administered with the metal chelator in a molar concentration from about 1:1 to about 5:1 metal chelator to methanobactin.

22. The method of claim 12 whereby the copper binding protein is administered in a pharmaceutically acceptable carrier.

23. A method of inhibiting oxygen radical formation comprising: administering to the animal an oxygen radical formation inhibiting amount of the copper binding protein of claim 1.

24. The method of claim 23 wherein the copper binding protein is administered in a dose of between about 0.1–1000 mg/kg/day.

25. The method of claim 24 wherein the copper binding protein is administered in a dose of between about 1–100 mg/kg/day.

26. A method of chelating copper comprising: administering a copper-chelating effective amount of the copper binding protein of claim 1.

27. The method of claim 26 wherein the copper binding protein is administered in a dose of between about 0.1–1000 mg/kg/day.

28. The method of claim 27 wherein the copper binding protein is administered in a dose of between about 1–100 mg/kg/day.

* * * * *